(12) United States Patent
Goroshevskiy et al.

(10) Patent No.: US 9,964,519 B2
(45) Date of Patent: May 8, 2018

(54) NON-DESTRUCTIVE SYSTEM AND METHOD FOR DETECTING STRUCTURAL DEFECTS

(71) Applicants: Valerian Goroshevskiy, Moscow (RU);
Svetlana Kamaeva, Moscow (RU);
Igor Kolesnikov, Moscow (RU)

(72) Inventors: Valerian Goroshevskiy, Moscow (RU);
Svetlana Kamaeva, Moscow (RU);
Igor Kolesnikov, Moscow (RU)

(*) Notice: Subject to any disclaimer, the term of this patent is extended or adjusted under 35 U.S.C. 154(b) by 0 days. days.

(21) Appl. No.: 15/403,476

(22) Filed: Jan. 11, 2017

(65) Prior Publication Data
US 2017/0122909 A1     May 4, 2017

Related U.S. Application Data

(63) Continuation-in-part of application No. 14/867,538, filed on Sep. 28, 2015, now Pat. No. 9,581,567, which
(Continued)

(51) Int. Cl.
*G01N 27/76*     (2006.01)
*G01N 27/82*     (2006.01)
(Continued)

(52) U.S. Cl.
CPC .......... *G01N 27/82* (2013.01); *B64C 39/024* (2013.01); *G01L 1/12* (2013.01); *G01L 1/125* (2013.01);
(Continued)

(58) Field of Classification Search
CPC ........ G01N 27/82; G01N 27/85; G01N 33/20; B64C 39/24; B64C 2201/123
See application file for complete search history.

(56) References Cited

U.S. PATENT DOCUMENTS 4,930,026 A * 5/1990 Kljuev .................. B23K 31/12
324/237
5,532,589 A * 7/1996 Gammell ............. G01N 27/825
324/226

(Continued)

*Primary Examiner* — Tung X Nguyen
*Assistant Examiner* — Dominic Hawkins
(74) *Attorney, Agent, or Firm* — Nadya Reingand; Yan Hankin

(57) ABSTRACT

A device for discovering, identification and monitoring, of mechanical flaws in metallic structures is disclosed, based on magneto-graphic/magnetic tomography technique to identify stress-related defects. The device can determine the position of the defect or stress including depth information. The device includes registration means that optimized for use with metallic structures of various types, shapes, and sizes. Applications include a real-time quality control, monitoring and emergency alarms, as well structural repairs and maintenance work recommendations and planning. Examples of the device implementation include pipes for oil and gas industry monitoring, detection of flaws in roiled products in metallurgical industry, welding quality of heavy duty equipment such as ships, reservoirs, bridges, etc. It is especially important for loaded constructions, such as pressured pipes, infrastructure maintenance, nuclear power plant monitoring, bridges, corrosion prevention and environment protection.

20 Claims, 5 Drawing Sheets

Related U.S. Application Data is a continuation-in-part of application No. 14/551,295, filed on Nov. 24, 2014, now Pat. No. 9,746,444, which is a continuation-in-part of application No. 13/920,216, filed on Jun. 18, 2013, now Pat. No. 9,176,096, which is a continuation-in-part of application No. 13/674,118, filed on Nov. 12, 2012, now Pat. No. 8,542,127, which is a continuation-in-part of application No. 13/662,427, filed on Oct. 27, 2012, now Pat. No. 8,447,532.

(51) Int. Cl.

| | | |
|---|---|---|
| *G01N 33/20* | (2006.01) | |
| *B64C 39/02* | (2006.01) | |
| *G01L 1/12* | (2006.01) | |
| *G01N 27/85* | (2006.01) | |
| *G01M 5/00* | (2006.01) | |
| *G01B 7/24* | (2006.01) | |
| *G01C 5/00* | (2006.01) | |

(52) U.S. Cl.
CPC ........ *G01M 5/0008* (2013.01); *G01M 5/0025* (2013.01); *G01M 5/0033* (2013.01); *G01M 5/0058* (2013.01); *G01N 27/85* (2013.01); *G01N 33/20* (2013.01); *B64C 2201/123* (2013.01); *G01B 7/24* (2013.01); *G01C 5/005* (2013.01)

(56) References Cited

U.S. PATENT DOCUMENTS

| | | | | |
|---|---|---|---|---|
| 6,023,986 | A * | 2/2000 | Smith | G01C 7/06 324/220 |
| 6,201,883 | B1 * | 3/2001 | Mizui | G01C 7/04 348/E13.008 |
| 8,554,462 | B2 * | 10/2013 | Lee | G05D 1/0202 382/106 |
| 2011/0060568 | A1 * | 3/2011 | Goldfine | G07C 3/00 703/6 |
| 2012/0119732 | A1 * | 5/2012 | Rose | G01N 29/2412 324/240 |
| 2012/0250010 | A1 * | 10/2012 | Hannay | G01N 21/952 356/237.1 |
| 2012/0262708 | A1 * | 10/2012 | Connolly | B64C 39/024 356/237.2 |
| 2012/0271461 | A1 * | 10/2012 | Spata | G01W 1/00 700/276 |
| 2013/0314084 | A1 * | 11/2013 | Lee | G01N 27/82 324/251 |

* cited by examiner

NON-DESTRUCTIVE SYSTEM AND METHOD FOR DETECTING STRUCTURAL DEFECTS

CROSS-REFERENCE TO RELATED APPLICATIONS

This application is a continuation-in-part of the U.S. patent application Ser. No. 13/920,216 filed on Jun. 18, 2013, published as US Patent Application Publication No. 20140368191 A1 and granted as U.S. Pat. No. 9,176,096 B2 and U.S. Pat. No. 8,542,127. This application is also a continuation-in-part of the U.S. patent application Ser. No. 14/551,295 filed on Nov. 24, 2014, published as US Patent Application No. 20160146758 A1. This application is also a continuation-in-part of the U.S. patent application Ser. No. 14/867,538 filed on Sep. 28, 2015, published as US Patent Application No. 20160231278 A1. U.S. patent application Ser. Nos. 11/920,216; 14/551,295; and 14/867,538 are hereby incorporated by reference.

BACKGROUND OF THE INVENTION

Field of the Invention

The present invention relates broadly to a non-destructive system and method for detecting structural defects as well as a device and method for continuous (extended) metallic structures inspection and monitoring for possible defects; in particular, to contact and non-contact magnetic scanner device and method, using magnetic tomography for a real-time structural defects detecting; assessment of mechanical stress and categorizing the defect by the level of danger.

Background Art

This invention can be used in various fields where constructions are tested for continuity defects and other stress concentrators as well as risk-level safety factors in a contact fashion or combined with the remote method. Examples of device and method implementation may include pipes for oil and gas industry, detection of flaws in rolled products in metallurgical industry, welding quality of heavy duty equipment such as ships and reservoirs, detection of defects in bridges or cell towers, etc. It is especially important for inspection of loaded constructions, such as pressured pipes, infrastructure maintenance, nuclear power plant monitoring, bridges, corrosion prevention and environment protection.

Railroads, electric transmission lines, bridges, cell towers, and pipelines have an important role in the nation's economy. These engineering structures do occasionally fail. Failure of these key infrastructure elements can cause economic disruption as well as put lives at risk.

Major causes of metallic infrastructure failure around the world are external interference, corrosion, and fatigue cracks; therefore, assessment methods are needed to determine the severity of such defects when they are detected in infrastructure, experiencing different loads.

Structures such as bridges, power transmission wires, wind turbines, and cell towers are important components of national infrastructure that require maintenance and examination for defects in order to allow detection of flaws that would result in failure. They are also all characterized in that these structures are often difficult to access due to their height, length, and sometimes the additional local loads they carry, i.e. bending, warping, exposure to wind, currents, etc. By mounting non-destructive non-contact detection sensors to a drone one can both conduct a thorough assessment of defects in the structure, rate the defects in terms of likelihood to cause structural failure and determine the priority and necessity of repairs and do this assessment without risk to human life as a drone equipped with sensors can access these places with greater ease than people can. For example, rather than lowering a bridge inspector on a crane bucket to examine the underside of a bridge a drone could be flown beneath the bridge and perform the inspection.

There are several magnetographic devices that have been disclosed for non-destructive inspection of ferrous materials. In magneto-graphic inspection and defectoscopy the tested area of the material is placed in proximity to the magnetic medium. The changes of the surface-penetrating impede flux due to the material flows or deviations can be recorded. The resulting "magnetogram" of the material can provide the information about the location, size, and type of the defect or abnormality. In general, this information can be convened into the report about the quality of the material. Obtaining the magnetogram (magnetic picture) of the material in the course of the non-destructive inspection process is very challenging and typically requires additional forms of inspection, such as roentgenogram or an X-ray image.

For example, U.S. Pat. No. 4,806,862 (Kozlov) offers a contact method of magnetographic inspection of quality of materials, where a magnetic substance (such as liquid) is applied to be magnetized together with the tested material. According to the invention, the intensity of the magnetizing field is established by the maximum curvature of the surface of a drop of a magnetic fluid applied onto the surface of the material to be inspected, so that the resulting magnetogram can be used to assess the quality of the material.

In another magnetographic U.S. Pat. No. 4,930,026 (Kljuev), the flaw sensor for magnetographic quality inspection is disclosed, which includes a flaw detector and a mechanism for driving the magneto-sensitive transducer. During the scanning procedure, the magnetic leakage fluxes penetrate through the surface of the material in place where flaws occur, resulting in a magnetogram of the tested material.

The deviations of F-value can be classified according to a level of mechanical stress concentration—as follows: X1—for negligible detects (good technical condition of the metal); X2—for defects that require planned repairs (acceptable technical condition); X3—for defects that require immediate repairs (unacceptable, pre-alarm technical condition, alarm).

The absolute values X1-X3 of the F-value (comprehensive value of magnetic field anomaly) should be defined for each particular case, depending upon the following factors: i) Material type (e.g. steel); ii) Topological location with the local background magnetic fields variation range, iii) Distance to the object (e.g. pipe-line installation depth), iv) General condition of the deformation-related tension within construction under testing, v) etc.

As a result, the only relative changes (variations) of the magnetic field can be evaluated, for the given defective segment (relatively to the flawless segment), by comparing to its relative F-values. Thus, the very moment of the ultimate stress-limit crossing can be identified for each defective segment during the real operation (i.e. under pressure/loaded) condition. It can be done by monitoring the development of the defects within its F-value interval, namely, starting from the good technical condition X1 up until the yield-strength limit approaching and material breakdown. It provides a real possibility to predict the defect's speed development, resulting in increased accuracy in priority order definition for upcoming maintenance steps.

The aforementioned techniques are not satisfactory to be used for efficient prediction in defects development timeline and not capable of providing a real-time alert about the strength-limits approaching, i.e. when probable construction failure is about to occur.

The closest remote technology to the disclosed invention is shown in RU 2264617 that describes the Magnetic Tomography (MT) technique. This technique includes a remote magnetic field vectors measurement in Cartesian coordinates with the movement of measuring device (magnetometer) along the pipe-line, the recording of the anomalies of magnetic field (on top of background magnetic field), processing of the data and report on found pipe-line defects with their localization shown in resulting magnetogram. The technique provides a good sensitivity, also capable of discovering the following types of defects: i) Changing in geometry: dents, wavy surface, deformed shape of cross-section; ii) Metal loss, having mechanical, technological or corrosion nature; material discontinuity: layering and inclusions; iii) Cracks; iv) Welding, flaws, including girth weld defects. Moreover, such method provides a risk-factor ranking of the discovered pipe-line defects accordingly to material tension concentration (factor F). Accordingly this technique was taken as initial prototype for the disclosed technology.

MT determines the comparative degree of danger of defects by a direct quantitative assessment, of the stress deformed state of the metal. Conventional surveys only measure the geometrical parameters of a defect. Their subsequent calculations to assess the impact of the defect on the safe operation of the pipe do not take into consideration the stress caused by the defect. Therefore conventional surveys may fail to detect dangerously stressed areas of the structure or, conversely, classify a defect as one which requires urgent attention when, in reality, the stress level may be low and the defect presents no immediate threat to the operation of the structure. Since MT directly measures the stress caused by defects it is an inherently more accurate guide to the safe operation of the structure than conventional survey methods.

There are several methods for integrity assessment of extended structures (e.g. metallic pipes) that have been proposed in literature. Thus, U.S. Pat. No. 4,998,208 (Buhrow, et al) discloses the piping corrosion monitoring system that calculates the risk-level safety factor producing an inspection schedule. There is another method disclosed in U.S. Pat. No. 6,813,949 (Masaniello, et al.), which addresses a pipeline inspection system having a serviceability acceptance criteria for pipeline anomalies, specifically wrinkles, with an improved method of correlating ultrasonic test data to actual anomaly characteristics.

The main disadvantages of previous methods are: i) The scope of its application is limited by large-scale linear objects and necessity to contact the surface. Located at a considerable distance from each other, ii) Difficult real-time implementation of the device, iii) It is impossible to identify the location of individual defects, visualize and specify the exact position on the internal or external tested surfaces; iv) There is also a lack of visualization of the obtained information in a form of the resulting tomogram where all the locations of the defective segments with associated respective risk factors (absolute mechanical stress values) are shown.

There is a need in developing a combination of contact and remote techniques in order to increase sensitivity, resolution and visual representation of the stress-related anomalies within the structure, as well as a probability of operation failure (i.e. risk-factor).

The defect areas risk-factor criteria and ranking (such as material stress: F-value) is used for planning a required sequence of repair and maintenance steps. Such criteria were developed by comparing a risk-factor calculated using the defect geometry in calibration bore pits with a predicted risk-factor obtained by the remote magneto-metric data (i.e. comprehensive F-value of particular magnetic anomaly).

In the traditional method, there is no evaluation of cracks stability, that is, no prognosis for the rate of crack-like defects development, especially in a longitudinal direction. There is also no evaluation of danger of other types of defects (e.g. welds) due to operation conditions, as the evaluation of metal properties degradation in aggressive conditions and with anomalies of stress-deformed state (SDS) is not carried out. For example, there are bridge sections with sags, bends, stresses/stretches/twists, that is, with loss of a bridge or pipes stability. In addition, the main problem—the degree of stress concentration in a particular bridge section—is not considered; it must be considered by engineers of the integrity department of the company/operator by e.g. expert evaluation, and it requires additional data about all local loads.

As an alternative to the above method, a magnetometric tomography method (MTM) has been proposed. MTM is a non-contact method of non-destructive testing (NDT) and technical diagnostics based on remote scanning the magnetic field of a ferro-magnetic structure in a system of orthogonal coordinates. Additionally, manual processing and calibrating are used to define locations of sections with metal defects of various types and other stress concentrators, identify the type of the most dangerous defects, and evaluate serviceability of defective sections according to the degree of mechanical stress concentration.

However, MTM is currently available only to pipeline based application (both on-shore and under water). Also the current, detection capability of such a magnetometer is only up to a maximum distance of 20 times the structural member diameter. Thus, such conventional MTM systems are not suitable for many structures, which may be located at significant height. The inspection speed is also limited to only about 2 meters per second (m/s), and the recording of distance is typically manual. Also, the analysis of the collected data is substantially manual, i.e. it relies again on expert evaluation.

A need therefore exists to provide a system and method for inspecting a structure with height or at altitude that seeks to address at least some of the above problems.

SUMMARY OF THE INVENTION

A device for discovering, identification of the danger level, risk-level safety factor and monitoring of mechanical concentrator (defects and loads) in extended metallic structure, such as pipe, a rail, a rolled metal product, a reservoir, a bridge, a vessel, a cable, electrical power transmission lines, or vertical pipelines, is disclosed. The device includes a pulse generator being used to irradiate a part of the metallic structure, a sensor array registering a response from this part of the structure, video camera, odometer, gyroscope, a GPS, and altimeter. The sensor array is located in proximity of the structure and measures its magnetic field gradient at a distance of up to 20 m from the structure without any surface preparation treatment. The sensor array includes a number of 3-component arrays, positioned along the 3 orthogonal dimensions. An analogue-to-digital converter digitizing the sensor signal which is wirelessly transmitted to the calculation unit.

A calculation unit exploits an inverse magnetostrictive (Villari) effect of changing material's magnetic susceptibility wider applied mechanical stress. Such changing results in gradient distribution of the magnetic field along the area of the structure that has a magnetic field anomaly. The distribution, in turn, reflects a presence and a value of the magnetic field anomaly at the given location. An absolute value of the mechanical stress, which corresponded to said anomaly, is further deducted, thus characterizing a defect of the structure and stress concentrators, optionally using, a pre-determined information such as look-up tables, standards, thresholds or an alternative contact measurement such as a contact probe.

The sensor array functions without removing the non-metallic cladding of the structure, such as a concrete wall around a metallic pipe, or paint and other non-corrosive layers around structural bridge components, for example. The sensor array measurements can also be performed from inside the pipeline.

The device detects foreign objects that are present in vicinity of the structure, measuring a relative distances and angles between themselves and the found anomaly. The discovered information is visualized by representing a topological map of the structure in real coordinates, showing simultaneously a structure layout, the foreign objects in vicinity, the location and calculated three-dimensional values of the mechanical stress.

The device is also capable of measuring a natural Earths background magnetic field without engaging the pulse generator. Such measurement is subtracted from the sensor signal to improve accuracy of the anomaly(s) location.

The device is operated by the battery with a residual charge indicator to ensure a quality and reliability of the identification in the field conditions and can perform without interruption of the structure normal operation.

A method for discovering, identification and monitoring of mechanical defects of various nature, causing the concentration of mechanical tension in metallic structures, is also disclosed. The method includes irradiating a part of the metallic structure with electromagnetic pulses, performing mechanical stress measurement of the metallic structure by a sensor array placed in proximity of the structure and producing a digitized sensor signal and digitizing the sensor signal. The method also includes analyzing the digitized signal in a calculation unit using the inverse magnetostrictive effect providing information about the presence and the value of the magnetic field anomaly caused by concentration of mechanical stress at the given location of the structure. The method calculates absolute values of the mechanical stress around the anomaly, thus unveiling and characterizing the defect of the structure or additional local loads.

Accordingly, the present invention is directed to a system and a method for inspecting a structure which makes it possible to inspect the structure at an altitude of 200 meters or more of a vertical structure or bridging structure with an accurate determination of the location of the defect area and its type. An object of the present invention is to provide a system for inspecting a structure, comprising: a drone mounted magnetometric tomography method (MTM) module movable adjacent the structure for detecting a defect along the structure; and means for determining a position, including altitude, of the drone mounted MTM module, thereby determining the position, including altitude, of the defect.

In one aspect of the present invention in the system the means for determining the position and depth of the drone mounted MTM module comprises means for determining the position and altitude of the drone mounted MTM module relative to a base station vehicle; and means for determining an absolute position of the base station vehicle and of the drone. In another aspect of the present invention in the system the means for determining the position including altitude of the drone mounted MTM module relative to the surface vessel comprises at least one of an odometer, a Doppler velocity log, a pressure sensor, an altimeter, a gyroscope, a video camera, and a microelectromechanical systems (MEMS) accelerometer coupled to the drone mounted MTM module. In another aspect of the present invention in the system the means for determining the absolute position of the drone and/or base station vehicle comprises a global positioning system (GPS) receiver. In another aspect of the present invention in the system time stamps of data from the drone mounted MTM module and the means for determining the position of the MTM module are synchronized based on a GPS time signal. In another aspect of the present invention the system further comprising means for categorizing the defect based on at least a density of magnetic field strength distribution along the axis of a structural member in an anomaly zone. In another aspect of the present invention in the system the means for categorizing the defect ranks the defect as one of one, two and three corresponding to immediate repair, scheduled repair and no repair, respectively. In another aspect of the present invention the system further comprising means for determining a safe operating parameter of the structure. In another aspect of the present invention in the system the drone mounted MTM module is disposed at least about 1 meter from the drone engines.

Another object of the present invention is to provide a method for inspecting a structure, the method comprising the steps of detecting a defect along the structure using a drone mounted magnetometric tomography method (MTM) module adjacent the structure; and determining a position of the drone mounted MTM module, thereby determining the position of the defect.

In one aspect of the present invention in the claimed method the step of determining the position of the drone mounted MTM module comprises: determining the absolute position of the drone mounted MTM module or the position of the drone mounted MTM module relative to a base station vehicle; and determining an absolute position of the base station vehicle. In another aspect of the present invention the method further comprising synchronizing time stamps of data from the drone mounted MTM module and equipment for determining the position of the drone mounted MTM module based on a GPS time signal. In another aspect of the present invention the method further comprising categorizing the defect based on at least a density of magnetic field strength distribution along a pipeline axis in an anomaly zone. In another aspect of the present invention the method further comprising ranking the defect as one of one, two and three corresponding to immediate repair, scheduled repair and no repair, respectively. In another aspect of the present invention the method further comprising determining a safe operating pressure of the pipeline. In another aspect of the present invention the method further comprising determining a safe operation term of the pipeline.

The present invention makes it possible to determine the exact location of the drone mounted MTM module on the structure when you move it in the air along the structure and thus pinpoint the location of the defect, if it is registered.

BRIEF DESCRIPTION OF THE DRAWINGS

The present invention will now be discussed in further detail below with reference to the accompanying figures in which.

DETAILED DESCRIPTION OF THE PREFERRED EMBODIMENTS

Figure 1:
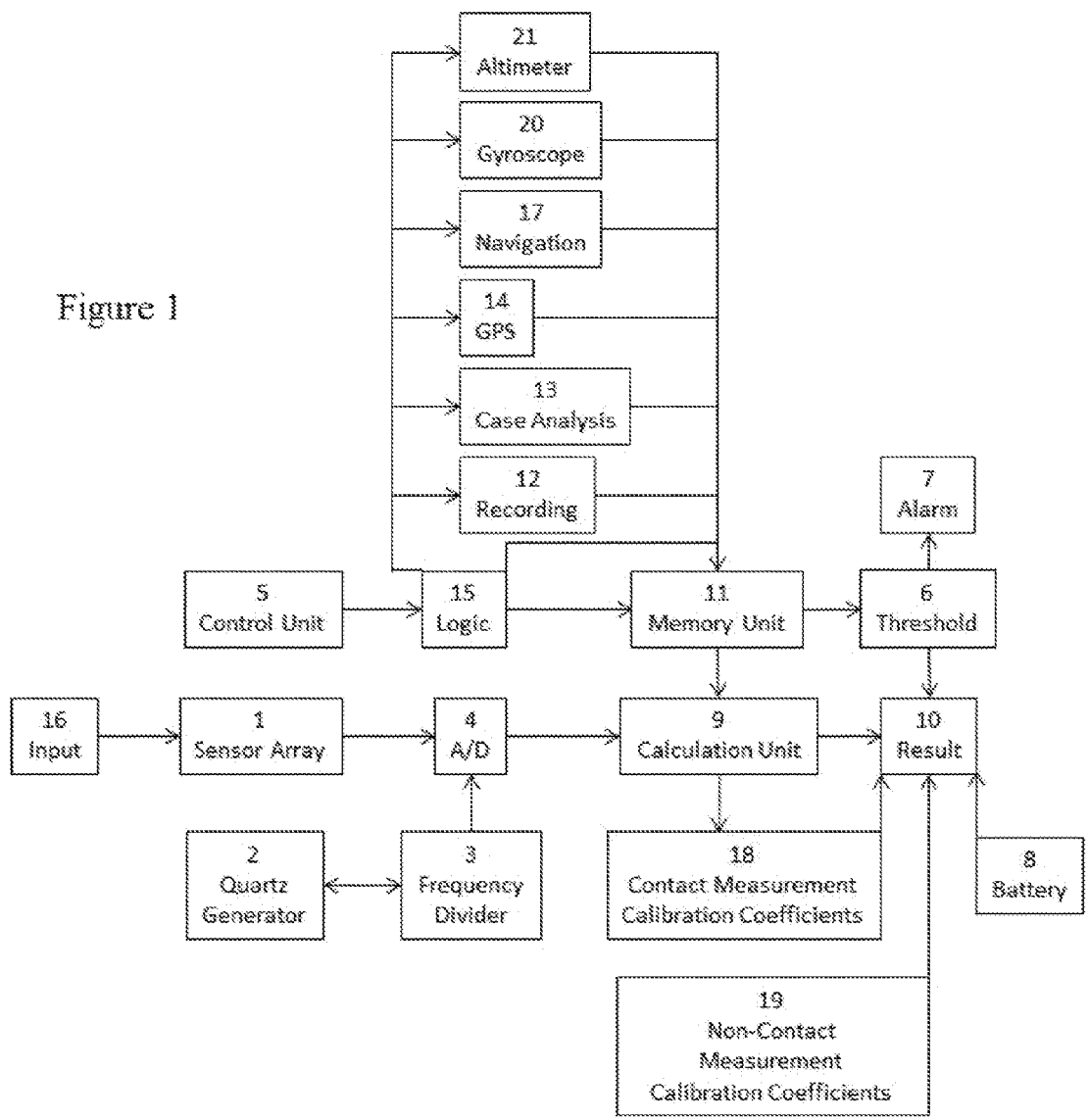
FIG. 1 shows a block-diagram of the device for discovering, identification and monitoring of mechanical defects in metallic structures using contact method, optionally, in combination with a non-contact technique.

The present invention describes the contact magnetic scanner device that uses a magnetic tomography (MT) for contact magnetographic identification and analysis of mechanical flaws/defects, optimized for extended metallic constructions inspection. The invention can be used in combination with a non-contact identification. And can be applied to variety of extended metallic structures, such as a pipe, a rail, a rolled metal product, as reservoir, a bridge, as vessel, a cell tower, a cable, or electrical power transmission lines.

The use of MT device has following advantages: 1) Applicable for inspecting structures that are otherwise difficult or dangerous to inspect; 2) the objects to be inspected include but not limited to: compressor stations, oil refineries, chemical plant pipelines, airport pipelines under concrete and asphalt pavement, pipeline inclusions, water-supply pipelines in cities, variety of extended metallic structures, such as a pipe, a rail, a rolled metal product, a reservoir, a bridge, a vessel, a cell tower, a cable, or electrical power transmission lines; 3) the use of MT device does not require any preparation of the structure for testing such as digging, cleaning, removing coatings, stopping fluid flow, or stopping structure operation; 4) the use of MT device does not require magnetizing of the object's structural members; 5) MT device capable of detecting flaws of various types including long crack-like structural member defects, fatigue cracks, stress cracking (SCC) and welding defects; 6) the use of MT device does not have limitation on the structure diameter or thickness, configuration and protective coatings, for example, change of pipe diameter/wall-thickness, turns and their directions, transported product (e.g. gas, oil, or water, electricity), inside pressure, pipeline protection e.g. cathodic protection, etc), type of cover (soil, water, asphalt, concrete, ice), etc, as well as structures in the housings (cartridges) of type "pipe in pipe" (if you can change the operating pressure in the inner tube—it is possible to distinguish between anomalies of the internal working of the pipe from the outside—housing).

The MT device is capable to evaluate the degree of danger of defects and risk safety factor by the level of concentration of mechanical tensions rather than defect geometry (e.g. length-width-depth) and particularly suitable for running a database on condition certification of objects of any length and any monitoring period.

The MT device implementation guarantees minimal customer resources use for monitoring preparation and repair works such as: i) reduces work volume and total costs of structure access works; ii) greatly reduces time of full diagnostic—repair evaluation—repair planning (fitness for service)—repair cycle; iii) gives structure corrosion and integrity prognosis and estimates levels of tense-deformed state of the structure under current operating conditions.

The MT device application provides a remote metal flaws monitoring, which is particularly suitable for hidden ferromagnetic constructions of extended length.

The general combined block-diagram of the method is given in FIG. 1.

The magnetic tomography device is based on using of the inverse magnetostrictive (Villari) effect—i.e. the changing of the material magnetic susceptibility under applied mechanical stress. Generally, such technique uses "natural" magnetization of the ferrous installations by magnetic field of the Earth. The changing of magnetic susceptibility results in distribution of magnetic field gradient along the structure surface area under measurement, thus providing information about the presence and the value of the magnetic field anomaly at the given location of the structure.

The term "contact measurement", as used herein is defined as the measurement being used from a small distance from the surface of the structure under testing. For the preferred embodiment of the invention, such distance is defined as a small if it is less than 20 cm from the surface of the structure. Furthermore, for the preferred embodiment of the invention applying an additional (pulsed) magnetic field is used.

The term "remote measurement", as used herein is defined as the measurement being used from a substantial distance from the structure under testing. Unlike to the contact measurement (non-destructive or distractive), the remote sensor is not necessary located in a close proximity to the structure. For the preferred embodiment of the invention, the substantial distance have value of 1-25 m, making the disclosed device especially effective for testing structures located deep underground, underwater, or at a significant height.

The remote measurement is capable of identifying the anomalies by deviation of the Earth's magnetic field at each location from a background value, without applying an additional magnetic field during the measuring.

The contact measurement device is also capable localizing coordinates of foreign objects in vicinity of the structure and making a linkage between the anomalies' locations and the foreign objects locations around the structure. In the preferred embodiment of the invention, the device finds coordinates of foreign objects which can be present in vicinity of the structure and measures a distance/angle between those foreign objects and the structure's anomaly.

Both remote and contact measurements are further capable of localizing coordinates of the structure and detecting anomalies with localized coordinates within the extended metallic structure based on measuring a value of the Earth's magnetic field at multiple locations in vicinity of the structure.

The present invention discloses the Contact Magnetic Scanner a device for the contact detection of the defects in metallic structures. The present invention effectively overcomes the aforementioned disadvantages of contact detect monitoring and detection.

Similarly to the remote method, the contact method at a given measurement point, the presence of the magnetic field anomaly and its magnitude (the local stress at the remote area) is determined based on a comparison between the increments (modules) of the Earth's magnetic field values (magnetic moments). Such calculation method is based on a dipole approximation of the remote stress-concentrator. The solution of the problem of the magnetic moment calculation results from a system of algebraic equations, which, for example, described in the U.S. Pat. No. 4,309,659.

The disclosed device expands the scope of device applications for different types of metallic structures (e.g. confined extended, small and large), ii) provided real-time operational means by including, data preprocessing and calibration, iii) increases the identification sensitivity of the defects located at the surface and within the volume of the object by including an additional pulse-magnetization unit, v) using a contact tomography technique in order to add 3D visualization capabilities using a 3D model of the tested object. The information visualization (display) unit of the device represents a topological map of the structure in real coordinates, showing; simultaneously a structure layout, the foreign objects in vicinity, the calculated values of a mechanical stress and the location of the found anomalies.

The disclosed device uses pre-determined information for structure anomaly identification and localizing. Such pre-determined information can be a look-up table, preset standards and thresholds, an alternative contact measurement, or combination of the above.

Moreover, the device can combine a contact and non-contact measurement increasing the reliability and accuracy of information about the necessary repair or stop alarm. It can be done using the risk-factor ranking tables based on the absolute values of stress, compared against the values from regulatory documentation (for particular object).

In the preferred embodiment of the invention, the device performs the identification of anomalies without interruption of the structure normal operation.

Increasing the efficiency of the method by applying a 3D visualization-assisted maintenance and repair schedule with the real values of mechanical stress) to the actual structural layout, such as a bridge integrated into the existing topology.

Such technological outcome can be achieved, mainly, due to the following innovative means: i) Contact (object surface) identification of the local defects and their respective risk-factors; ii) Comparing the remote measurement with ones obtained locally; iii) Comparing the resulting measurements against the values from regulatory documentation (for the particular object), iii) Graphical 3D visualization of the obtained information using the actual topological layout of the area and the structure in absolute geographical coordinates.

For the remote registration of magnetic field anomalies in extended metallic structures (such as a bridge) is performed in a predetermined coordinate system relatively to the structure with a known (fixed) remote sensor array aperture. The coordinates of each single measurement along the structure can be chosen accordingly to the cross-section size and burial depth or height of the structure. It results in the matrix distribution of magnetic field gradient along the structure surface area under each single measurement. The presence and the value of the magnetic field anomaly at the given location are derived from the comparison of different increments of the Earth's magnetic induction vector modulus.

Similarly to the remote measurements, the contact measurement also includes device to measure the magnetic field vector in Cartesian coordinates, by moving the registration device (magnetometer) along (above, below, or to the side of) the metallic structure (of arbitrary configuration, in general) and registration of the magnetic field anomalies. Such anomalies are calculated by a deviation from the background values (calculated using matrix transformations).

The contact device also connected the data recording unit and decoding system that provides conclusive information about the presence and location of the defects in the form of magnetograms that shows the location of the defective pipe sections and their degrees of risk.

Similarly to the remote measurements, the contact measurement of the extended object (such as bridge) uses the recording of the magnetic field that is carried out in a pre-defined coordinate system at specifically defined measuring points by a set of sensors having a pre-selected aperture (base) K2. This aperture corresponds to the axis of the extended object with a measuring step K1.

The exact location of measurement points is defined from the width and height (e.g. of the bridge), using coefficients K1, K2 and K3, where: K1—is the measuring step (registration of the magnetic field induction) 0.2 in, for example, K2—the aperture (the base) of the sensors, chosen from the ratio $0.7 D \leq K 2 \leq l$, 4 D, where D—is the diameter or width of the structure (pipeline), K3—is the depth or height of the structure, or the shortest distance from the metallic construction to the surface. [m].

In the case of a non-linear (or small) extended object the contact registration c the magnetic field is carried out in a fixed coordinate system. In this case, registration is possible at different relative positions of the sensors and their arbitrary orientation with respect to the object (coplanar or collinear).

To verify the anomaly angular position along the structure (pipeline) circumference, the angular scanning step K1 should not larger than 30 degrees with the pre-defined distance between the sensors K2, to ensure the required accuracy of calculations.

The block-diagram of such device is shown in FIG. 1, with the reference to FIG. 1, the device for contact and, optionally, non-contact measurements comprises of a sensor array for remote measurements (1), a sensor array for proximity (contact) measurements (20), a quartz generator (2), a frequency divider (3), analogue-to-digital converter (A/D) (4), a control unit (5), a threshold unit (6), a light- and sound-alarm unit (7), a battery with a charge indicator (8), a calculation unit (9), a (resulting) information unit (10) with a display unit (23), a non-volatile memory unit (11), a recording unit (12), a case-analysis unit (13), a pulse generation lint (21), an odometer unit (23), a GPS unit and pressure sensor(s) (14), navigation unit (accelerometer/odometer) (17), gyroscope (20), altimeter (21) and a logic unit (15). The device performs in a following manner.

The remote sensor array (1) registers induction gradients of the magnetic field (16) within construction under testing.

The proximity sensor array registers induction gradients of the magnetic field, the gradients corresponding to reflections of the EM pulses from the structure; the EM pulses generated by the Pulse generator. The signal from the proximity sensor is used as a calibrating measurement.

By using A/D converter (4), the both digitized signals (remote and contact) are: i) inputted into calculation unit as a preliminary data; ii) recorded by the memory unit (11). The Quartz generator (2) controls the frequency of the A/D converter (4).

The control unit (5) through the logic unit (15) controls the case analysis unit (13) with predetermined database and lookup tables, the recording unit (12), the GPS unit (14), the navigation unit (17), gyroscope (20), altimeter (21) and the memory unit (11).

The calculation unit (9) receives the information from units (12), (13), (14), (17), (10), (21) through the memory unit (11), controlled by logic unit (15).

The real-time information from (4) is compared with the information from the threshold unit (6). By these means, the visualization of the real-time data against the threshold values is provided, enabling the alarming (by the unit (7)) an operator about potentially dangerous operational conditions of the structure. The remaining charge of the battery (8) is monitored. The calculation unit (9) is responsible for the information processing, providing the information to the resulting, and visualization unit (10).

The calculation unit (9) unit receives the digitized signal, uses the inverse magnetostrictive effect of changing of material magnetic susceptibility under applied mechanical stress resulting in gradient distribution of the magnetic field along an area of the structure that has a magnetic field anomaly, the distribution of magnetic field gradient providing an information about a presence and a value of the magnetic field anomaly at the given location of the structure and a mechanical stress, corresponded to the anomaly.

The calculation unit (9) further calculates absolute values of a mechanical stress around all found anomalies in the metallic structure using, the measured values of the Earths magnetic field for each anomaly and applying the calibration coefficient. As a result, the calculation unit is capable of identifying and localizing of said signal anomalies.

In one embodiment of the invention the calculation unit is located at a distance from the sensor array, and the digitized signal is transmitted to the calculation unit via wireless connection.

The measured magnetic field values from 2 inputs (16) and (19) local stress at the remote area are recorded at each measurement point, (both for contact and optional remote sensor independently), then further compared with other measurements within a respective segment of the metallic construction. By these means the anomalies (levels of stress-deformation) that deviate from the baseline magnetic field values are selected. Thus, the location of each stress-related deformation is derived from the maximum concentration value of the magnetic field after comparing it with the previous measurements.

The visualization unit has a 3-dimensional display means in order to provide a 3-D representation of the density of magnetic field strength distribution, found detects and its risk-factors along with the topological (3D) map of the structure under testing.

The resulting and visualization unit (10) also accommodates inputs from the threshold unit (6) and the light-/sound-alarm unit (7) which enables identification of the parameters' deviation from the background level, as well as (e.g. wirelessly) informing an operator about the deviation value in real-time, respectively.

Moreover, the resulting and visualization unit (10) is capable of comparing the remote signals (19) with in-contact measurement (18) and producing a set of calibration coefficients in order to calibrate the resulting calculated data of found magnetic anomalies.

The situational case-analysis unit (13) enables the analysis of the information in the context of pre-determined technological information and schemes, which, in combination with the GPS unit, navigation unit, gyroscope, and altimeter sensor(s) (14, 17, 20, 21), provides more accurate topological mapping.

In the preferable configuration of the device, a GPS sensor (14) is complemented by a navigation unit (17) and gyroscope(s) (20) and/or set of accelerometer(s) (17), and odometer unit (17) enabling the recording of the device's angle-positioning relatively to the extended metallic structure cross-section at each moment of the magneto-graphical measurements. The recorded angle-positioning data (including positioning, relatively to horizon) is used further to correct the magneto-graphical measurements due to structural bending/turning-related deviations.

Accordingly, the absolute coordinates of discovered defects relatively to the (visible) reference objects can be obtained with the following registration in the database during the equipment assessment report.

In the preferable configuration of the mentioned device, each sensor arrays (1) and (19) consist of a few 3-compenent arrays, positioned along the 3 orthogonal dimensions. Alternatively, each array includes a few single-component sensors, such as optically pumped quantum analyzers. Using the optically pumped quantum analyzers in the sensor array (1) allows higher flaw-detection accuracy in underground constructions, well-suited for detecting relatively small values of mechanical stress, and/or deeper underground installation.

Since sensor arrays (1) and (19) can be rotated above the surface of the structure during the scanning procedure, it is possible to implement a polar coordinate system for detects detection, in combination with the data from the gyroscope (20) and navigation/accelerometer/odometer unit (17).

The recording process is arranged in a discrete manner, enabling an independent storage and access for different recorded portions (memory segments) of the scanning.

In the preferable configuration of the disclosed device, the calculation unit (9) calculates: i) magnetic field gradients distributed along the square area within the defined segment of the structure, ii) the values of the local mechanical stress within the defined segment of the structure.

The device allows identifying the location of defects using both in-contact and remote magnetic measurements.

Moreover, it expresses the calculations in real-time, also providing the visualization of the information in the form of tomograms with reference to the 3D model of the controlled object.

Moreover, the device provides automated evaluation of the defects risk factor at respective identified location, allows automatic processing, interpretation and archiving of non-destructive testing results.

In the alternative configuration of the disclosure, the calculation unit (9) can be realized similarly to the U.S. Pat. No. 4,309,659.

Moreover, in the alternative configuration of the disclosure, the recording unit (12) can be realized similarly to the RU2037888 patent.

Figure 2:
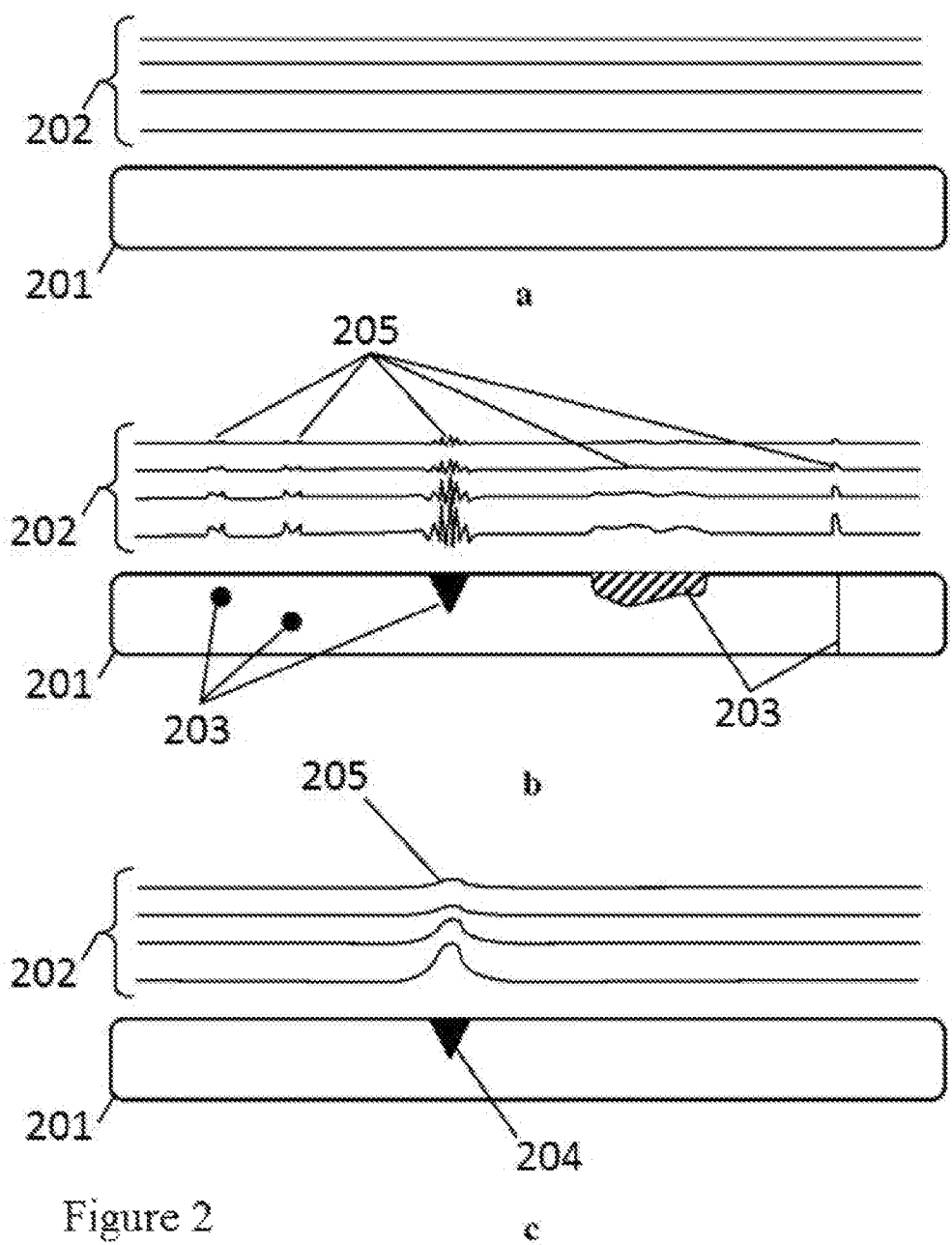
FIG. 2 shows a general principle of operation of the contact and non-contact magneto-graphic techniques used in metallic structure defects monitoring and integrity assessment.

The principle of operation of the device shown in FIG. 1, is explained further in FIG. 2. The FIG. 2a shows the structure (201) without defects, with the preliminary magnetic tomography charts (magnetogram) (202) showing the measured background (calibrated to zero) level of magnetization. The FIG. 2b shows the same structure (201) with the potential defects (203), (204) corresponded to the deviations of the tomography charts (205). The FIG. 2c show the same structure (201) with the processed tomography charts (205) showing the location of the defect (204) that require an immediate attention (unacceptable, pre-alarm technical condition, alarm), based on the local mechanical stress value estimate.

As mentioned before, the magnetogram (202) attributes and characterizes the section of the structure by registering and analyzing changes in the magnetic field of the structure such as a bridge. These changes are related to stress, which, in turn, is related to defects in the metal and insulation. Magnetic measurements data is collected from the surface and includes the detected anomalies. Such detected anomalies are function of a local stress and/or local mechanical tension and structural changes in the metal. Moreover, a post-processing of this experimental data enables the visualization of the flaws in the structure.

The device can operate on the metallic structure which is covered by a non-metallic cladding and the sensor array performs the measurement without removing the cladding. Moreover, the device (sensor array) is capable of performing measurements from within the structure, such as between bridge beams and girders.

The described MT device does not measure the dimensions of geometric defects alone, but, instead, provides a stress measurement caused by these defects and identifies their character, location and orientation in accordance with the location and orientation of the area of stress. Linear and angular coordinates of flaws in the metal and coating have been experimentally defined within a tolerance of +/−0.25 m.

The device explained by FIG. 1 and FIG. 2 can effectively identify and analyze the magnetic field anomalies in areas with stress concentrators caused by: i) defects or changes in structural conditions (such as metal loss, cracks, dents, lamination and inclusions); ii) erosion, seismic activity, or third-party damage.

Figure 3:
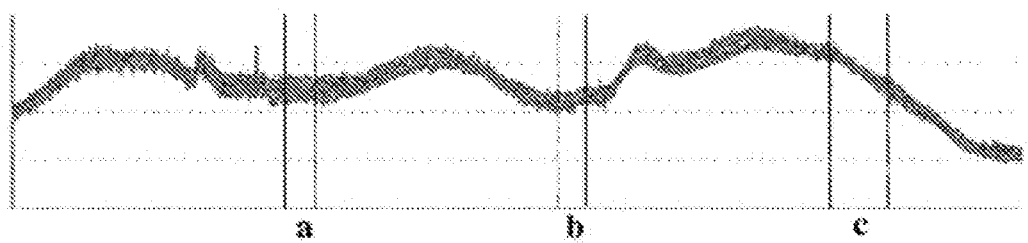
FIG. 3 shows an example of a single magneto-graphic measurement. The diagram represents the three areas of a magnetic field anomalies (a), (b) and (c) corresponding to the respective local mechanical stresses. The area (c) shows the evidence of the metal stress yielding-limit crossing.

FIG. 3 shows the example of a single magneto-graphic measurement. The diagram represents the three areas of a magnetic field anomalies (a), (b) and (c) corresponding to the respective local mechanical Stresses. The area (c) shows the evidence of the metal stress yielding-limit crossing.

In parallel, the in-contact (proximity) defectoscopy has been performed at the location (c). The actual dimensions of defects (cracks and corrosion) have been evaluated. The magnetographic device calibration has been done based on a difference between the measured signal (versus background) and the actual parameters of the defect(s) found. Then, the calibrated values of the anomalies have been used as a criterion. For this particular case, the calibrated values appeared to be 3-10 times higher comparing to the background signal value. The follow-up magnetographic measurements has been performed in a real-time.

the presented MT device helps to plan necessary structural maintenance procedures and define their priorities. The device is particularly efficient when the magneto-graphic material (Magnetic Tomography) inspection is applied to extended metallic constructions, revealing its flaws against the topological map of the structure.

Moreover, the device enables direct monitoring of the defective construction segments with still acceptable technical conditions. It allows a long-term database support for the follow up monitoring, certification, prognosis and operational timeline for the structure.

Figure 4:
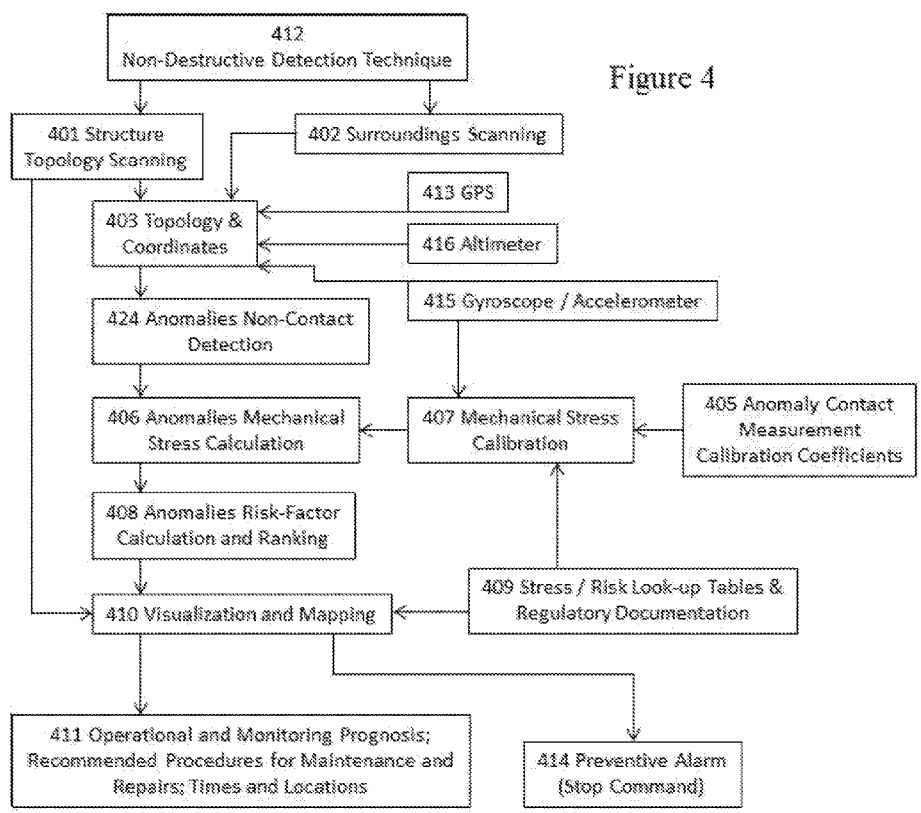
FIG. 4 shows a block-diagram for metallic structure integrity assessment and maintenance planning method.
Figure 5:
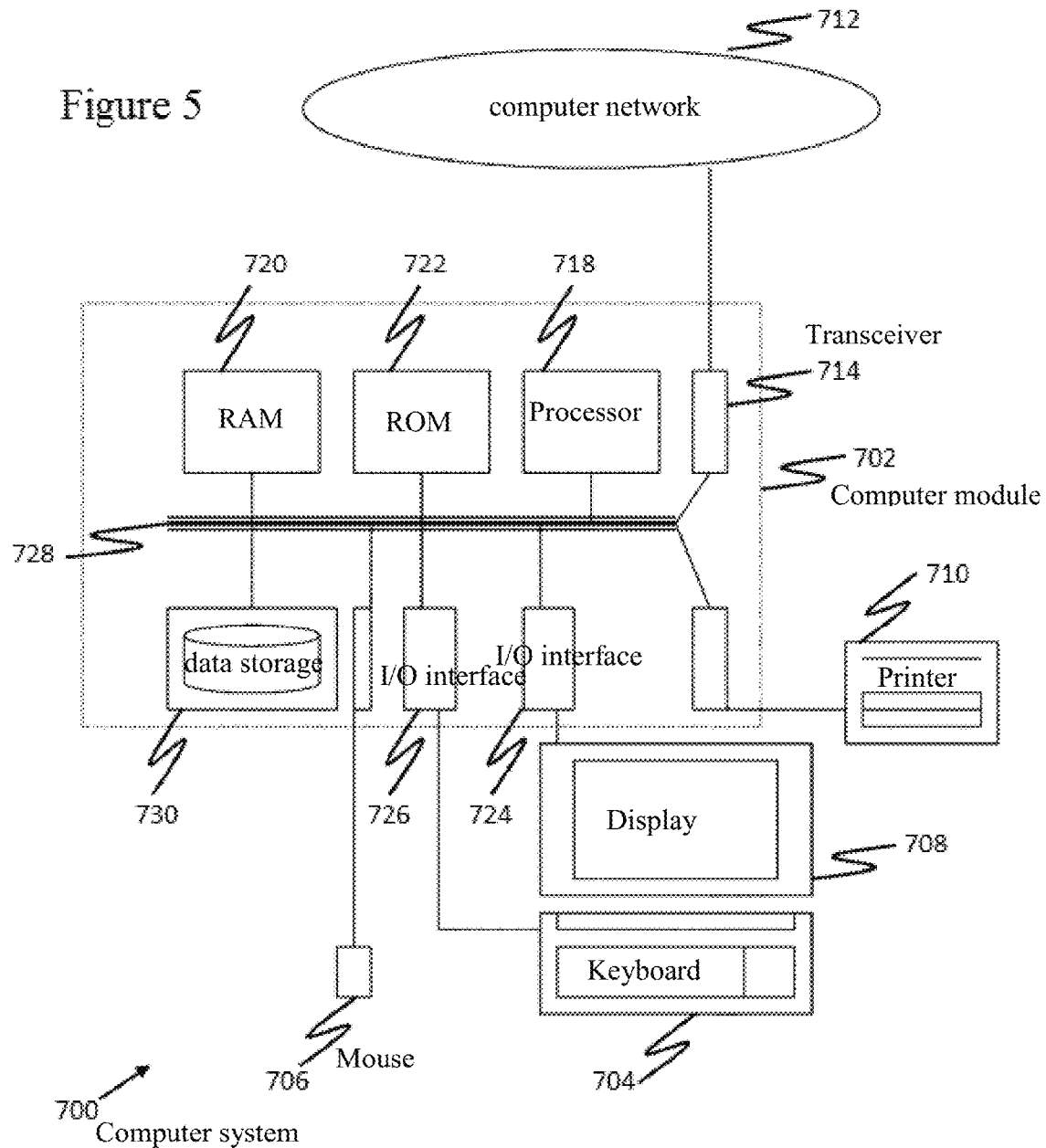
FIG. 5 shows at block diagram illustrating a computing device for implementing the method and system of the example embodiment.

The present invention also describes the magnetographic method maintenance timeline planning method (priority steps), optimized for extended metallic constructions. The block-diagram of the method is given in FIG. 4.

The method includes (with reference to FIG. 4): Precise scanning (401) using the non-destructive magneto-graphic (such as MT) anomalies detection technique (412) for (axial) localization of the extended metallic structure (e.g. subterranean or submarine pipeline), as well as surrounding scanning (402) for identification of other possible objects in the vicinity of the structure, including hidden objects (pipes, cables) detection (424) and identification of the defective segments or areas of the said structure, in general, by using thermo-visual imaging, magneto-graphic methods or by other remote (non-contact, non-destructive) methods; accurate location of different types of anomalies by using thermal and magnetic non-contact scanning sensors moving in Cartesian coordinates. Registering and processing of the obtained data and assessing resulting anomalies in accordance with their risk-factor and structural topology (mapping) (403). Identification of the absolute geographical coordinated for characteristic elements of the construction under testing (403), preferably by using a GPS sensor(s) (413) and altimeter (416) and (inertial) navigation system (gyroscope and/or accelerometers) (415). Non-contact detection (424) of the construction defects and flawless segments. In-contact measurement of at least one found defect (405) (e.g. visual, spectral, magneto-graphic). Calculation of the local metal stress at each found anomaly (406) and calibration (407), using calibrating coefficients obtained by in-contact method (405) and regulatory documentation and stress/risk look-up tables (409). Processing the obtained information about discovered defects and its ranking accordingly to the risk factor (value of mechanical stress) (408). Graphical visualization of the results in the form of the topological map of the construction using absolute values of geographical coordinates (410). The topological map would reflect the maintenance schedule to be applied to the construction following from the recorded mechanical stress values at the defective segments of the construction (409), (410). The method includes preventive warning means (414) to inform about defects that require immediate attention. e.g. unacceptable operational condition. The aforementioned method provides operational and monitoring prognosis (411) with an optimal priority planning for required maintenance steps for construction under testing.

In the preferred embodiment of the invention the non-destructive detection of anomalies in the structure is performed using magnetographic technique such as MT.

The main goals of the present invention are: i) to increase the method's applicability area: ii) to increase the accuracy of the priority scheduling for required maintenance and repair procedures iii) to broaden the spectrum of the potentially scheduled repair procedures, based on the additional data.

The invention is a system for inspecting a structure which has a drone mounted magnetometric tomography method (MTM) module for detecting a defect or stress along the structure; an altimeter sensor for determining a height of the drone mounted MTM module.

The system further having a module with a sensor array with at least three sensor positioned in three orthogonal dimensions.

The system further having a compass for registering azimuth data of the defect and stress position on the structure at the determined height.

The system wherein the system outputs a 3D map of the inspected structure on a computer screen; the map showing the defects and stress concentrator.

The system further having means for categorizing the defect and condition stress effect based on at least a density of magnetic field strength distribution along a structure axis in an anomaly zone.

The system further having a camera for registering an image of the defect, which is visible or non-destructive testing (NDT) or non-destructive examination (NDE) tools for hidden defects (например, internal corrosion) and causes of additional loads (e.g., free slack or loading landslides in the mountains).

The system further having additional means for determining a position, including height via altimeter sensor, of the drone mounted MTM module relative to a sea surface and relative to a linear coordinate of structure axis comprising, at least one of an odometer, a Doppler velocity log and a microelectromechanical systems (MEMS) accelerometer coupled to the drone mounted MTM module.

The system further having an engine for moving the sensors along the structure adjacent to the structure.

The system wherein a distance between the sensors and a surface of the structural member is from 0, being on the surface of the structural member, to a distance equal to 15 times a diameter (up to 25 m) or width of the structural member.

The system further having a range finder to determine a distance between the sensors and the surface of the structural member.

The system further having a control unit to adjust operation of the engine in order to keep the distance between the sensors and the surface of the structural member from 0, being on the surface of the structural member, to a distance equal to 15 times a diameter or width of the structural member.

The system further having a processing unit.

The system wherein the means for categorizing the ranging of dangerous as one of one, two and three corresponding to immediate repair, scheduled repair and no repair, respectively taking account stress concentration, stress effect, material strength, condition stress effect, or stressing sequence.

The system further having means for determining a safe operating parameter of the structure, taking into account stress concentration, stress effect, material strength, condition stress effect, or stressing sequence.

The system further having means for determining a safe operation term of the structure.

The system wherein the drone mounted MTM module is mounted to a remotely operated drone.

The system wherein the drone mounted MTM module is disposed at least about 1 meter from drone engines.

The invention also providing a method for inspecting a metallic structure, the method comprising the steps of detecting a defect or stressing along the structure using a drone mounted magnetometric tomography method (MTM) module adjacent the structure; determining a height of the drone mounted MTM module by use of an altimeter sensor; and determining, a position, including height via altimeter sensor, of the drone mounted MTM module, thereby determining the position, including height via altimeter sensor, of the defect or stress concentrators.

The method wherein the step of determining the position, including height via altimeter sensor, of the drone mounted MTM module comprises: determining the position, including height via altimeter sensor, of the drone mounted MTM module relative to a base station vehicle or absolute position of the drone mounted MTM.

The method further involving synchronizing time stamps of data from the drone mounted MTM module and equipment for determining the position, including height via altimeter sensor, of the drone mounted MTM module based on a GPS time signal.

The method further involving categorizing the defect based on at least a density of magnetic field strength distribution along a structure axis in an anomaly zone.

The method further involving ranking the defect as one of one, two and three corresponding to immediate repair, scheduled repair and no repair, respectively.

The system further involving monitoring and automatic alarm control emergency shutdown (ESD) in situation with the destination of deformations of Yield Stress, Specified Minimum Yield Stress (SMYS), yield strain, Ultimate Tensile (UT) Strength, Rupture Pressure Ratio (RPR), buckling stress, fatigue limit under cyclic loading for fatigue cracks, or stress corrosion crack or cracking (SCC).

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof it will be appreciated that a variety of programming languages and coding thereof may be used to implement the teachings of the disclosure contained herein. Moreover, the computer program is not intended, to be limited to any particular control flow. There are many other variants of the computer program, which can use different control flows without departing, from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Table 1 shows details of the navigation data in the example embodiment.

TABLE 1

| Field | Description |
| --- | --- |
| DD/mm/yy | date |
| Hh:mm:ss.ss | 1PPS GPS time |
| XF.xx | Easting of drone |
| YF.yy | Northing of drone |
| SF.xx | KP of drone (Distance along the structure) |
| CFF | Drone height |
| XVV.x | Drone heading |
| sDVVV | CP Values (Controlled Parameter) |

Table 2 shows details of the magnetometric data in the example embodiment.

TABLE 2

| Field | Description |
| --- | --- |
| DD/mm/yy | date |
| Hh:mm:ss.ss | 1PPS GPS time |
| $H_x$ | X-axis magnetometric value |
| $H_y$ | Y-axis magnetometric value |
| $H_z$ | Y-axis magnetainetric value |

If an anomaly in the magnetometric data is found at the same time stamp, such anomaly is associated with the coordinates that have been determined. By compiling and processing all data collected from an inspection mission, locations of potential defects, which correspond to the anomalies in magnetometric data, are determined in the example embodiment.

Furthermore, the system of the example embodiment is capable of evaluating a danger degree of a defect, calculating a pipeline safe operating pressure and calculating a structure safe operation term. An integral index F of danger degree of a defect that takes into account the extent of magnetic anomaly, amplitude and shape of distribution of magnetic field intensity vector over the background values is calculated in the example embodiment based on the following formula:

$$F = A \cdot e^{\hat{}}(1 - Q_\phi/(Q_{AH})) \quad (1)$$

where A denotes a corrective coefficient characterizing influence of defects of pipelines upon the magnetic field change and is typically determined after a calibration procedure; $Q_{AH}$, $Q_\phi$ denote density of magnetic field strength distribution along a structure axis in anomaly zone and in a "calm" background area $A/_m$, respectively. The density is typically determined as a length of a section of a curve.

In the example embodiment, the curve comprises a geometrical place of points of intensity of a magnetic field in space, thus:

$$dQ = \sqrt{\text{square root over}(dH_x^2 + dH_y^2 + dH_z^2)} \quad (2)$$

where $dH_x$, $dH_y$, $dH_z$ denote values of change of magnetic field strength vector. $A/_m^2$, respectively.

In the example embodiment, $Q_{AH}$ and $Q_\phi$ are calculated by integrating dQ by length of anomaly and d background sections, respectively.

The calculated values of index F are maintained e.g. in a database of revealed defects, and also in diagrams of anomalies distribution. Table 3 provides a ranking of sites (i.e. locations) with magnetic anomalies based their danger degree. On sites with the first danger rank, the first priority repair-reconstruction works are carried out. On sites with the second danger rank, planned repair-reconstruction works are scheduled. On sites with the third danger rank, the operation of the pipeline is allowed without repair-reconstruction works.

TABLE 3

| No | Value of integral index F | Danger degree of magnetic anomaly, rank |
| --- | --- | --- |
| 1 | from 0 to 0.2 | first |
| 2 | from 0.22 to 0.55 | second |
| 3 | from 0.55 to 0.99 | third |

Additionally, in the example embodiment, the safe operating parameter $P_{safe}$ is calculated based on the respective danger degree of the defect. The parameter can be stress, rust, stress fractures, corrosion, pressure, or another parameter.

For sections with defects of the first danger rank (i.e. $0 \leq F < 0.2$), at $F < 0.1$:

$$P_{safe} = 0.9 \, P_{oper} + 0.1 \, P_{oper} \cdot F \quad (3)$$

at $0.1 \leq F < 0.2$: $P_{safe} = 0.9 \, P_{oper} + 0.05 \, P_{oper} \cdot F$ (4)

For sections with defects of the second danger rank (i.e. $0.2 \leq F < 0.55$):

$$P_{safe} = 0.1 \, P_{oper} + 0.05 \, P_{oper} \cdot F \quad (5)$$

For sections with defects of the third danger rank (i.e. $F \geq 0.55$):

$$P_{safe} = 1.06 P_{oper} + (0.95 P_{design} - 1.06 P_{oper}) \cdot F \quad (6)$$

where $P_{oper}$ denotes parameter in a structure at the moment of inspection, measured in megapascals (MPa); $P_{design}$ denotes design parameter in a structure (in MPa); and $P_{safe}$ denotes calculated safe operating parameter in a structure.

If the value of calculated safe operating parameter $P_{safe}$ exceeds the design parameter $P_{design}$, the structure is preferably operated at the design parameter. The assessment of structure technical condition can also be carried out based on the coefficient of safe parameter—estimated repair factor—ERF (ASME), where:

$$\text{ERF} = P_{oper}/P_{safe} \quad (7)$$

In the example embodiment, at ERF≥1, a defect is assessed as extreme and subject to the first priority repair.

For a structure short-term operation, the maximum admissible operating parameter $P_{max}$ (also known as MAOP) is calculated in the example embodiment:

$$P_{max} = P_{safe} \cdot \tau \quad (8)$$

where τ denotes a coefficient of the short-term increase of the parameter, which is determined by the operating organization and may range from 1.1 to 1.15 in the example embodiment.

The structure safe (i.e. accident-free) operation term $T_{safe}$ is calculated in the example embodiment on the condition that the structure is operated at the calculated safe parameter, as described above with respect to Equations (3)-(6). After having repaired all revealed defects the structure safe operation term is fixed no more than 90% from calculated value lease explain what is meant by "fixed no more than 90% from each revealed defect, the calculations are carried out in the example embodiment by the following formula:

$$T_{safe} = K_p \cdot K_F \cdot K_t \tag{9}$$

where $K_p$ denotes a coefficient considering the pressure in the structure, $K_F$ denotes a coefficient considering danger degree of a defect; and $K_t$ denotes a coefficient which takes into account the term of a structure operation.

For example, if the structure is operated at the design parameter, $K_p=1$, otherwise:

$$E\hat{\delta} = e\ 1 - P_{design} P_{oper} \tag{10}$$

Also, $K_F = -2\ Lg\ 1 - F$ (11)

$K_t$ considers the influence of operation factors in particular, the probability of is structure failure within the first 3 years of operation because of construction-assembly detects and because of corrosion damage after 5-7 years of operation.

$$K_t = 10 \cdot T \cdot \Delta T \tag{12}$$

where T denotes the normative operation term of a structure (measured in years), and $\Delta T$ denotes the operation term of a structure since the moment of its putting into operation (measured in years).

Additionally, the method and system of the example embodiment can have a high sensitivity due to the non-contact registration of the structure magnetic field and the filtration of relevant signal over noise. This means that metal detects causing stress-deformed conditions are typically not missed during inspection. Advantageously, the magnetic field change of the whole defective section (cluster)—not a separate defect—is registered in the example embodiment. That is the method and system of the example embodiment can provide a quantitative assessment of stress concentrator F for all interconnected defects of the registered magnetic anomaly (or stress-deformed condition anomaly resulting from a cluster).

Furthermore, the method and system of the example embodiment can advantageously be a single tool for inspection of structures of different sizes, and allow evaluating the danger degree of defects of various types on the basis of the unified quantitative index F of stress-concentrator value. Preferably, this allows calculating ERF for the defects of "metal loss" type and other types such as "crack-like defects", weld defects, "continuity failure", "geometry change", etc. Thus, the calculations of serviceability for all types of defects—not only "metal loss" type—can be made possible.

Figure 6:
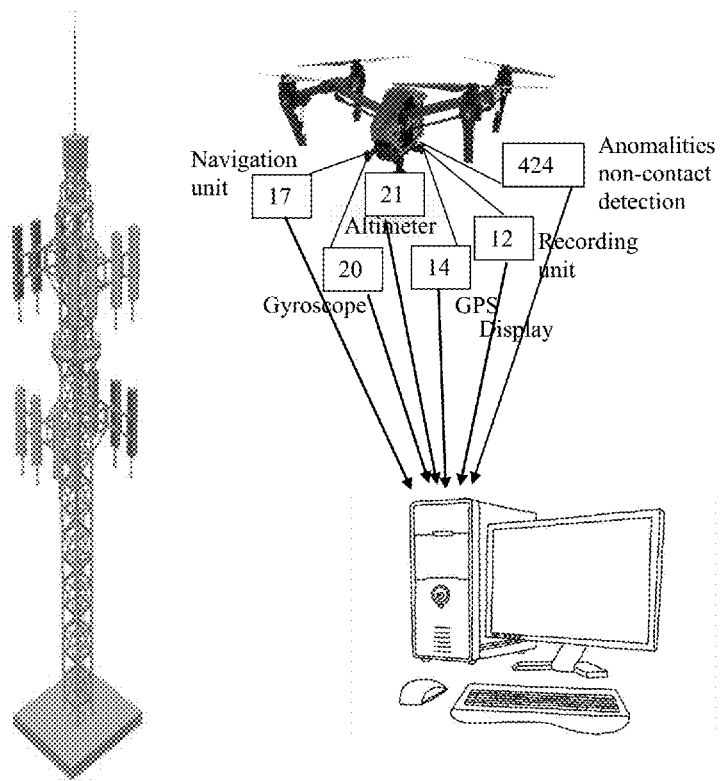
FIG. 6 shows a general schematics of a drone mounted system for inspecting a structure having a movable drone mounted MTM module; an altimeter sensor, and a calculation unit.

The method and system of the example embodiment can be implemented on a computer system (700), schematically shown in FIG. 6. It may be implemented as software, such as a computer program being executed within the computer system (700), and instructing the computer system (700) to conduct the method of the example embodiment.

The computer system (700) comprises a computer module (702), input modules such as a keyboard (704) and mouse (706) and a plurality of output devices such as a display (708), and printer (710).

The computer module (702) is connected to a computer network (712) via a suitable transceiver device (714), to enable access to e.g. the Internet or other network systems such as Local Area Network (LAN) or Wide Area Network (WAN).

The computer module (702) in the example includes a processor (718), a Random Access Memory (RAM) (720) and a Read Only Memory (ROM) (722). The computer module (702) also includes a number of Input/Output (I/O) interfaces, for example I/O interface (724) to the display (708), and I/O interface (726) to the keyboard (704).

The components of the computer module (702) typically communicate via an interconnected bus (728) and in a manner known to the person skilled in the relevant art.

The application program is typically supplied to the user of the computer system (700) encoded on a data storage medium such as a CD-ROM or flash memory carrier and read utilising a corresponding data storage medium drive of a data storage device (730). The application program is read and controlled in its execution by the processor (718). Intermediate storage of program data maybe accomplished using RAM (720).

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. A drone mounted system for inspecting a ferro-magnetic structure, comprising:
   a. a movable drone mounted magnetometric tomography method (MTM) module for detecting a defect or stress along the ferro-magnetic structure; the MTM module performing measurement of defect characteristics including magnetostriction; a gradient of magnetic field in the defect and magnetic susceptibility;
   b. an altimeter sensor for determining a height of the drone mounted MTM module to locate the defect, and
   c. a calculation unit for categorizing the defect with a ranging of dangerous as one of one, two, and three corresponding to immediate repair, scheduled repair, and no repair.

2. The system as claimed in claim 1, wherein the module comprises a sensor array with at least three sensor positioned in three orthogonal dimensions.

3. The system as claimed in claim 2, further comprising a compass for registering azimuth data of the defect and stress position on the structure at the determined height.

4. The system as claimed in claim 2, the system outputting a 3D map of the inspected structure on a computer screen; the map showing the defects and stress concentrator.

5. The system as claimed in claim 2, wherein the calculation unit is located in the module.

6. The system as claimed in claim 5, wherein the calculation unit is in wireless communication with the module.

7. The system as claimed in claim 6, further comprising a camera for registering an image of the defect, which is visible or non-destructive testing (NDT) or non-destructive examination (NDE) tools for hidden defects and internal anomalies, including corrosion, weld cracs, and delaminations.

8. The system as claimed in claim 7, wherein the calculation unit is further configured to account for stress concentration, stress effect, material strength, condition stress effect, or stressing sequence.

9. The system as claimed in claim 7, wherein the calculating unit determines a safe operating parameter of the structure.

10. The system as claimed in claim 1, wherein the calculation unit determines a safe operation term of the structure.

11. The system as claimed in claim 2, further comprising a global positioning system (GPS) unit and/or a height sensor for determining a position of the drone mounted MTM module relative to a ground surface or a structure surface and relative to a linear coordinate of structure axis comprising at least one of an odometer, a Doppler velocity log and a microelectromechanical systems (MEMS) accelerometer coupled to the drone mounted MTM module.

12. The system as claimed in claim 1, wherein a distance between the sensors and a surface of the structure is from 0, being on the structure surface, to a distance equal to 15 time a diameter or a width of the structure or a structural member of the structure.

13. The system as claimed in claim 12, further comprising a range finder to determine a distance between the sensors and the surface of the structure.

14. The system as claimed in claim 13, further comprising a control unit to adjust operation of the engine in order to keep the distance between the sensors and the surface of the structure from 0, being on the structure surface, to a distance up to 30 meters.

15. The system as claimed in claim 1, further comprising a control unit to adjust operation of an engine of the drone mounted MTM in order to keep the distance between the sensors and the surface of the structure from 0, being on the structure surface, to a distance equal to 15 time a diameter of the structure.

16. The system as claimed in claim 1, further comprising monitoring an automatic alarm control ESD in situation with the destination of deformations of Yield Stress, Specified Minimum Yield Stress (SMYS), yield strain, Ultimate Tensile (UT) Strength, Rupture Pressure Ratio (RPR), buckling stress, fatigue limit under cyclic loading for fatigue cracks, or stress corrosion crack or cracking (SCC).

17. A method for inspecting a Ferro-magnetic structure, the method comprising the steps of:
   a. detecting a defect or stressing along the structure using a drone mounted magnetometric tomography method (MTM) module adjacent to the ferromagnetic structure; the MTM module performing measurement of defect characteristics including magnetostriction; a gradient of magnetic field in the defect and magnetic susceptibility;
   b. determining a height of the drone mounted MTM module by use of an altimeter sensor;
   c. determining a position of the drone mounted MTM module, thereby determining the position of the defect or stress concentrators, and
   d. categorizing a danger of the defect as one of one, two, and three corresponding to immediate repair, scheduled repair, and no repair.

18. The method as claimed in claim 17, wherein the step of determining the position of the drone mounted MTM module comprises:
   a. determining the position of the drone mounted MTM module relative to a ground surface or a structure surface; and
   b. determining an absolute position of the drone mounted MTM.

19. The method as claimed in claim 18, further comprising synchronizing time stamps of data from the drone mounted MTM module and equipment for determining the position of the drone mounted MTM module based on a GPS time signal.

20. The method as claimed in claim 19, further comprising categorizing the defect based on at least a density of magnetic field strength distribution along a structure axis in an anomaly zone.

* * * * *